US009572984B2

(12) United States Patent
Hou et al.

(10) Patent No.: US 9,572,984 B2
(45) Date of Patent: Feb. 21, 2017

(54) SYSTEM AND METHOD FOR COUPLING BURST AND TONIC STIMULATION

(71) Applicant: PACESETTER, INC., Sylmar, CA (US)

(72) Inventors: Wenbo Hou, Santa Clarita, CA (US); Xiaoyi Min, Camarillo, CA (US); Stuart Rosenberg, Castaic, CA (US)

(73) Assignee: Pacesetter, Inc., Sylmar, CA (US)

( * ) Notice: Subject to any disclaimer, the term of this patent is extended or adjusted under 35 U.S.C. 154(b) by 267 days.

(21) Appl. No.: 14/563,895

(22) Filed: Dec. 8, 2014

(65) Prior Publication Data

US 2016/0158550 A1 Jun. 9, 2016

(51) Int. Cl.
*A61N 1/36* (2006.01)
*A61N 1/05* (2006.01)

(52) U.S. Cl.
CPC ......... *A61N 1/36071* (2013.01); *A61N 1/0551* (2013.01); *A61N 1/36178* (2013.01)

(58) Field of Classification Search
CPC ............ A61N 1/36071; A61N 1/36135; A61N 1/36139; A61N 1/36171; A61N 1/0551
See application file for complete search history.

(56) References Cited

U.S. PATENT DOCUMENTS

| 8,295,939 | B2 | 10/2012 | Jacobson | |
|---|---|---|---|---|
| 8,364,273 | B2 | 1/2013 | De Ridder | |
| 2011/0184486 | A1* | 7/2011 | De Ridder | A61N 1/36071 607/45 |
| 2011/0313483 | A1* | 12/2011 | Hincapie Ordonez | A61B 5/04001 607/17 |

FOREIGN PATENT DOCUMENTS

WO 2012155187 A1 11/2012

OTHER PUBLICATIONS

Betts, R.P. et al, "Nerve fibre velocity and refractory period distributions in nerve trunks," Journal of Neurology, Neurosurgery, and Psychiatry. 1976;39:694-700.
Parker, John L et al., "Compound action potentials recorded in the human spinal cord during neurostimulation for pain relief," Pain. 2012;153:593-601.
Rhodes, Paul A. et al., "A model of thalamocortical relay cells," J Physiol. 2005;563(3):765-781.
Crosby, Nathan D. BS et al., "Optimization of Burst Spinal Cord Stimulation in a Rat Model of Neuropathic Pain," Dept of Bioengineering, University of Pennsaylvania, Philadelphia, PA. pp. 1-26.

* cited by examiner

*Primary Examiner* — Edward Moran
*Assistant Examiner* — Natasha Patel

(57) ABSTRACT

A system and method for delivering coupled burst and tonic stimulation of nervous tissue is provided. The system and method includes providing a lead with at least one stimulation electrode configured to be implanted at a target position proximate to nervous tissue of interest. The system and method further includes coupling the lead to an implantable pulse generator (IPG). The method delivers a first current pulse configured as a tonic stimulation waveform to the at least one electrode. The tonic stimulation waveform is configured to excite A-beta fibers of the nervous tissue. After a tonic-burst delay, the IPG delivers second current pulses configured as a burst stimulation waveform to at least one electrode. The burst stimulation waveform is configured to excite C-fibers of the nervous tissue.

20 Claims, 8 Drawing Sheets

SYSTEM AND METHOD FOR COUPLING BURST AND TONIC STIMULATION

FIELD OF THE INVENTION

Embodiments of the present disclosure generally relate to neurostimulation (NS) systems, and more particularly to coupling burst and tonic stimulation signals in connection with pain relief.

BACKGROUND OF THE INVENTION

Spinal cord stimulation (SCS) is used to treat a wide range of chronic neuropathic pain conditions by delivering electrical stimulation to select portions of the spinal cord. In the past, SCS therapy has been proposed in which a tonic therapy is delivered having continuous pulses have a select frequency, pulse width and intensity. By way of example, tonic therapies have been proposed to manage cervical and lumbar pain. The frequency, pulse width and intensity may be changed, along with electrode configuration and placement on the spinal column in connection with pain relief for individual patients.

NS systems are devices that generate electrical pulses and deliver the pulses to nervous tissue to treat a variety of disorders. For example, spinal cord stimulation has been used to treat chronic and intractable pain. Another example is deep brain, stimulation, which has been used to treat movement disorders such as Parkinson's disease and affective disorders such as depression. While a precise understanding of the interaction between the applied electrical energy and the nervous tissue is not fully appreciated, it is known that application of electrical pulses to certain regions or areas of nervous tissue can effectively mask certain types of pain transmitted from regions, increase the production of neurotransmitters, or the like. For example, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

An NS system has been proposed in WO 2012/155187, titled "Method and Apparatus for Application of a Neural Stimulus," to John Parker at al. According to an aspect, the '187 application provides a method of applying a neural stimulus to yield a therapeutic effect while suppressing psychophysical side effects by delivering a first stimulus to recruit a portion of the A-beta fiber population and a second stimulus, delivered within the refractory period following the first stimulus, to recruit a further portion of the A-beta fiber population. The '187 application describes stimulation at successively larger and larger pulse amplitudes to recruit successively more A-beta fibers. The '187 application describes that pulses are timed so that later pulses occur in the refractory period of excited A-beta fibers from the previous pulse in order that different subpopulations of the A-beta fibers can be selected with each pulse.

However, in at least some patients, it may not be desirable for tonic stimulation to induce paresthesia. For example, paresthesia causes discomfort and irritation in many patients. Therefore, in many instances, it is not preferable to deliver stimulation at successively larger and larger pulse amplitudes.

Moreover, while burst therapies may be used to reduce neuropathic pain without generating paresthesia, limited information is known regarding the relation between neuropathic pain and various aspects of burst therapy. Further, limited information is known regarding the relation between management of pain therapy and coupled operation of tonic and burst therapies.

SUMMARY

In accordance with one embodiment, a method for simultaneous burst and tonic stimulation of nervous tissue is provided. The method includes providing a lead having at least one stimulation electrode on the lead to be implanted at a target position proximate to nervous tissue of interest, and coupling the lead to an implantable pulse generator (IPG). The method delivers a first current pulse configured as a tonic stimulation waveform to the at least one electrode. The tonic stimulation waveform is configured to excite A-beta fibers of the nervous tissue. After a tonic-burst delay, the method delivers second current pulses configured as a burst stimulation waveform to at least one electrode. The burst stimulation waveform is configured to excite C-fibers of the nervous tissue. The tonic-burst delay is adjusted between the tonic and burst stimulation waveforms to deliver the burst stimulation waveform during a refractory period of the A-beta fibers excited by the tonic stimulation waveform to avoid excitation of the A-beta fibers excited by the tonic stimulation waveform. Optionally, the method includes the current pulses of the burst stimulation waveform being delayed by a predetermined initial delay following the current pulse of the burst stimulation waveform, the predetermined initial delay representing the tonic-burst delay and being programmed by a clinician. Optionally, the method includes the tonic stimulation waveform representing a biphasic waveform and the burst stimulation waveform represents a series of monophasic pulses.

Optionally, the method provides a tonic stimulation waveform which is biphasic with first and second phase pulses, the first phase pulse being configured to capture at least a portion of the A-beta fibers to deliver a first pain relief, the second phase pulse being configured to repolarize charge at a stimulation site to limit excitation of A-beta fibers.

Optionally, the method further comprises sensing signals at the at least one electrode on the lead, and analyzing the signals to identify a C-fiber sensory action potential (C-fiber SAP) component of the signals. Optionally, the method further comprises adjusting the tonic-burst delay based on the C-fiber SAP component of the signals.

Optionally, the method provides for an adjusting operation which includes adjusting the tonic-burst delay to reduce the C-fiber SAP component. Optionally, the method further comprises analyzing a feature of interest from a morphology of the C-fiber SAP component over time, counting a number of occurrences of the feature of interest that occur within the C-fiber SAP component over a predetermined duration, comparing the number of occurrences to a prior number of occurrences, and adjusting the tonic-burst delay based on the comparing operation. Optionally, the method further comprises analyzing the C-fiber SAP component to determine SAP activity level data for a present coupled tonic-burst therapy.

Optionally, the method provides for the at least one electrode comprising a plurality of electrodes; and wherein the delivering operation comprises delivering the tonic stimulation waveform to a first sub-set of the electrodes and the burst stimulation waveform to a second sub-set of the electrodes, the first and second sub-sets have at least one unique electrode relative to each other. Optionally, the method provides for the at least one electrode including a microelectrode located immediately adjacent C-fibers, the method further comprising sensing a C-fiber sensory action potential (SAP) directly at the microelectrode and performing an iterative feedback loop to adjust at least one therapy parameter for a coupled tonic-burst therapy based on the C-fiber SAP.

In accordance with another embodiment, a system for coupling burst and tonic stimulation is provided, which comprises a lead having at least one stimulation electrode, the lead configured to be implanted at a target position proximate to nervous tissue of interest; and an implantable pulse generator (IPG) coupled to the lead. The IPG is configured to deliver a first current pulse configured as a tonic stimulation waveform to the at least one electrode, the tonic stimulation waveform configured to excite A-beta fibers of the nervous tissue. The IPG is also configured to, after a tonic-burst delay, deliver second current pulses configured as a burst stimulation waveform to at least one electrode, the burst stimulation waveform configured to excite C-fibers of the nervous tissue. The IPG is also configured to adjust the tonic-burst delay between the tonic and burst stimulation waveforms to deliver the burst stimulation waveform during a refractory period of the A-beta fibers excited by the tonic stimulation waveform to avoid excitation of the A-beta fibers excited by the tonic stimulation waveform.

Optionally, the system may be configured wherein the lead includes a plurality of electrodes, and the IPG is configured to deliver the tonic stimulation waveform to a first sub-set of the electrodes and the burst stimulation waveform to a second sub-set of the electrodes, the first and second sub-sets have at least one unique electrode relative to each other. Optionally, the system may be configured wherein the at least one electrode includes a microelectrode located immediately adjacent C-fibers, the method further comprising sensing a C-fiber sensory action potential (SAP) directly at the microelectrode and performing an iterative feedback loop to adjust at least one therapy parameter for a coupled tonic-burst therapy based on the C-fiber SAP.

Optionally, the system further comprises sensing signals at the at least one electrode on the lead, and analyzing the signals to identify a C-fiber sensory action potential (C-fiber SAP) component of the signals. Optionally, the system further comprises adjusting the tonic-burst delay based on the C-fiber SAP component of the signals. Optionally, the system provides the adjusting operation including adjusting the tonic-burst delay to reduce the C-fiber SAP component. Optionally, the system further comprises analyzing a feature of interest from a morphology of the C-fiber SAP component over time, counting a number of occurrences of the feature of interest that occur within the C-fiber SAP component over a predetermined duration, comparing the number of occurrences to a prior number of occurrences, and adjusting the tonic-burst delay based on the comparing operation.

Optionally, the system further comprises analyzing the C-fiber SAP component to determine SAP activity level data for a present coupled tonic-burst therapy. Optionally, the system is configured wherein the at least one electrode comprises a plurality of electrodes; and wherein the delivering operation comprises delivering the tonic stimulation waveform to a first sub-set of the electrodes and the burst stimulation waveform to a second sub-set of the electrodes, the first and second sub-sets have at least one unique electrode relative to each other.

DETAILED DESCRIPTION

Figure 1:
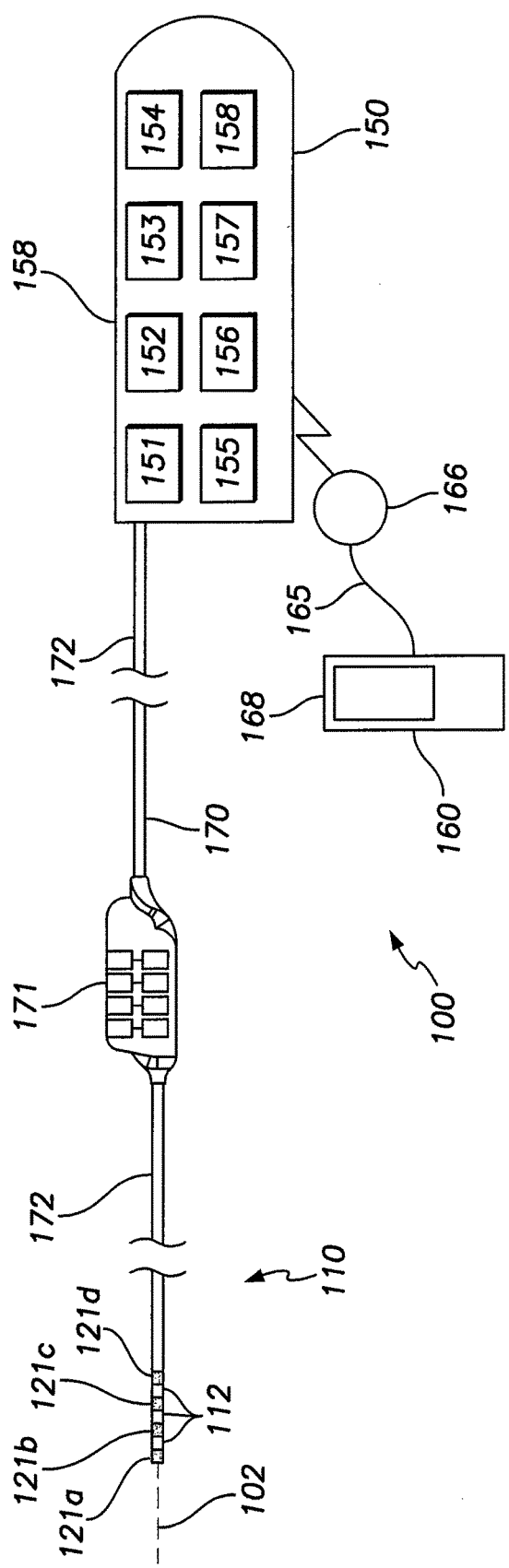
FIG. 1 illustrates a neurostimulation system, according to an embodiment of the present disclosure.

Embodiments described herein include neurostimulation (NS) systems and methods for generating simultaneous tonic and burst stimulation waveforms using the same. The NS lead may be configured to be inserted into a space or cavity of a patient and positioned adjacent to nervous tissue of interest. In certain embodiments, the NS lead includes wireless leads that are positioned entirely within an epidural space of a spinal column.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

In accordance with embodiments described herein, methods and systems are provided that utilize a unique coupled tonic/burst therapy, where a tonic stimulation waveform is followed by a burst stimulation waveform timed into the refractory period of the A-beta fiber action potential. In accordance with embodiments herein, the methods and systems afford desirable pain relief efficacy while conserving battery power.

Nervous System Overview

The nervous system is comprised of the central nervous system (CNS) and the peripheral nervous system (PNS). The CNS contains the brain and spinal cord. The PNS is comprised mainly of mixed nerves, which are enclosed bundles of the long fibers or axons (endings of nerve cells or neurons) that connect the CNS to every other part of the body. There are two types of nerve fibers in a mixed nerve that include: sensory nerve fibers (afferent fibers sending information towards the brain) and motor nerve fibers (efferent fibers sending information from the brain). Sensory neurons transmit information from the environment, such as pain and motor neurons that mediate voluntary and involuntary movement.

In general, the peripheral nerve fibers may be classified into three types or groups of nerve fibers based on the nerve fiber diameter and conduction velocity, namely A-, B- and C-fibers. A fibers have large diameters, high conduction velocities, are highly myelinated, and are further subdivided by size and conduction velocity as A-alpha, A-beta, A-gamma and A-delta fibers. By way of example, the fast conduction velocity of the A-alpha fibers may be on the order of 80-120 m/s, and the A-alpha fibers may be on average 13-20 µm in diameter. B-fibers have diameters of about 3 µm and conduction velocities of 3-15 m/s. C-fibers are small neurons with slow conduction velocities and are not myelinated. A-delta fibers have conduction velocities on the order of 5-35 m/s, and the A-delta fibers may be on average 1.0-5.0 µm in diameter. A-delta fibers carry information mainly from the nociceptive-mechanical or mechanothermal-specific stimuli and are considered nociceptors. Their receptive fields (area of innervation) are small, and therefore, provide precise localization of pain.

The B group fibers are moderately myelinated with a small diameter. Generally, the B group fibers are the preganglionic-fibers of the autonomic nervous system and have a low conduction velocity. By way of example, the conduction velocity of the B group fibers may be on the order of 3-14 m/s.

C-fibers are unmyelinated, have a small diameter and low conduction velocity. By way of example, the slow conduction velocity of the C-fibers may be on the order of 0.5-2.0 m/s, and the C-fibers may be on average 0.2-1.5 µm in diameter. C-fibers carry sensory information, such as nociception (pain), temperature and itch. C-fibers are unmyelinated unlike most other fibers in the nervous system. The lack of myelination is, at least in part, a cause of the slow conduction velocity attributed to C-fibers.

C-fibers are activated by and carry information from a variety of high-intensity mechanical, chemical and thermal stimulation and thus are considered as polymodal nociceptors. C-fibers comprise about 70% of all the fibers carrying noxious input. The receptive field of these neurons is large and, therefore, less precise for pain localization.

The cell bodies of all primary afferent pain neurons from the body, face, and head are located in the dorsal root ganglia (DRG) and in the trigeminal ganglia respectively. Some of these cell bodies have myelinated axons (A-delta fibers), and others have unmyelinated axons (C-fibers). Both A-delta fiber's and the unmyelinated C-fiber's axons have free nerve endings, which innervate the same areas in the periphery.

A-delta fibers are responsible for the sensation of a quick shallow pain that is specific on one area, termed as first pain. The A-delta fibers respond to a weaker intensity of noxious stimulus. C-fibers respond to noxious stimuli which have stronger intensities and account for the slow, but deeper second pain that spreads out over an unspecific area.

Refractory Period

The refractory period is the time interval during which a nerve fiber is incapable of conducting another impulse after a conditioning stimulus (intrinsic or externally induced). Following the passage of an impulse, an axon becomes totally unexcitable for a period time, such as a fraction of a millisecond. During the unexcitable time period, the membrane is still depolarized from the preceding action potential and another stimulus will generally not initiate a fresh impulse in this region, nor can an impulse generated elsewhere passes through this area. Neither excitability nor conductivity, therefore, is present. The reason for this refractoriness is that shortly after the action potential is initiated, the sodium channels become inactivated, and any stimulus applied to these channels at this point will not re-open the inactivated gates unless the membrane is repolarized either to, or almost to, the original resting membrane potential level. Because of the refractory period, a nerve fiber cannot be stimulated continuously, thus, the refractory period acts to limit the rate at which nerve impulses can be conducted.

System Overview

FIG. 1 depicts an NS system 100 that generates electrical pulses for application to tissue of a patient according to one embodiment. For example, the NS system 100 may be adapted to stimulate spinal cord tissue, peripheral nervous tissue, deep brain tissue, cortical tissue, cardiac tissue, digestive tissue, pelvic floor tissue, or any other suitable nervous tissue of interest within a patient's body.

The NS system 100 includes an implantable pulse generator (IPG) 150 that is adapted to generate electrical pulses for application to tissue of a patient. The IPG 150 typically comprises a metallic housing or can 158 that encloses a controller 151, pulse generating circuitry 152, a charging coil 153, a battery 154, a far-field and/or near field communication circuitry 155, battery charging circuitry 156, switching circuitry 157, memory 158 and the like. The controller 151 typically includes a microcontroller or other suitable processor for controlling the various other components of the device. Software code is typically stored in memory of the IPG 150 for execution by the microcontroller or processor to control the various components of the device.

The IPG 150 may comprise a separate or an attached extension component 170. If the extension component 170 is a separate component, the extension component 170 may connect with the "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within connector portion 171 or within the IPG header for electrical connection with respective connectors. Thereby, the pulses originating from the IPG 150 are provided to the leads 110. The pulses are then conducted through the conductors of the lead 110 and applied to tissue of a patient via stimulation electrodes 121a-d that are coupled to blocking capacitors. Any suitable known or later developed design may be employed for connector portion 171.

The stimulation electrodes 121a-d may be positioned along a horizontal axis 102 of the lead 110, and are angularly positioned about the horizontal axis 102 so the stimulation electrodes 121a-d do not overlap. The stimulation electrodes 121a-d may be in the shape of a ring such that each stimulation electrode 121a-d continuously covers the circumference of the exterior surface of the lead 110. Each of the stimulation electrodes 121a-d are separated by non-conducting rings 112, which electrically isolate each stimulation electrode 121a-d from an adjacent stimulation electrode 121a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121a-d may be configured to emit the pulses in an outward radial direction proximate to or within a stimulation target. Additionally or alternatively, the stimulation electrodes 121a-d may be in the shape of a split or non-continuous ring such that the pulse may be directed in an outward radial direction adjacent to the stimulation electrodes 121a-d. The stimulation electrodes 121a-d deliver tonic and burst stimulation waveforms as described herein. The electrodes 121a-d may also sense sensory action potential (SAP signals) for a data collection window. The current pulses of the burst stimulation waveform are delayed by a predetermined initial delay following the current pulse of the burst stimulation waveform, the predetermined initial delay representing the tonic-burst delay and being programmed by a clinician. The tonic stimulation waveform is biphasic with first and second phase pulses, the first phase pulse configured to capture at least a portion of the A-beta fibers to deliver a first pain relief, the second phase pulse configured to repolarize charge at a stimulation site to limit excitation of A-beta fibers. The at least one electrode comprises a plurality of electrodes; and wherein the delivering operation comprises delivering the tonic stimulation waveform to a first sub-set of the electrodes and the burst stimulation waveform to a second sub-set of the electrodes, the first and second sub-sets have at least one unique electrode relative to each other.

The at least one electrode includes a microelectrode located immediately adjacent C-fibers, the method further comprising sensing a C-fiber sensory action potential (SAP) directly at the microelectrode and performing an iterative feedback loop to adjust at least one therapy parameter for a coupled tonic-burst therapy based on the C-fiber SAP.

The lead 110 may comprise a lead body 172 of insulative material about a plurality of conductors within the material that extend from a proximal end of lead 110, proximate to the IPG 150, to its distal end. The conductors electrically couple a plurality of the stimulation electrodes 121a-d to a plurality of terminals (not shown) of the lead 110. The terminals are adapted to receive electrical pulses and the stimulation electrodes 121a-d are adapted to apply the pulses to the stimulation target of the patient. Also, sensing of physiological signals may occur through the stimulation electrodes 121, the conductors, and the terminals. It should be noted that although the lead 110 is depicted with four stimulation electrodes 121a-d, the lead 110 may include any suitable number of stimulation electrodes 121a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for all embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

Figure 2C:
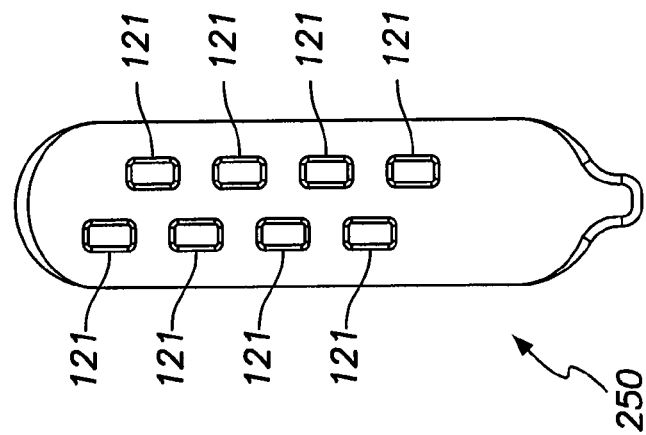
FIGS. 2A, 2B, and 2C illustrate stimulation portions at distal ends of various lead embodiments.
Figure 2B:
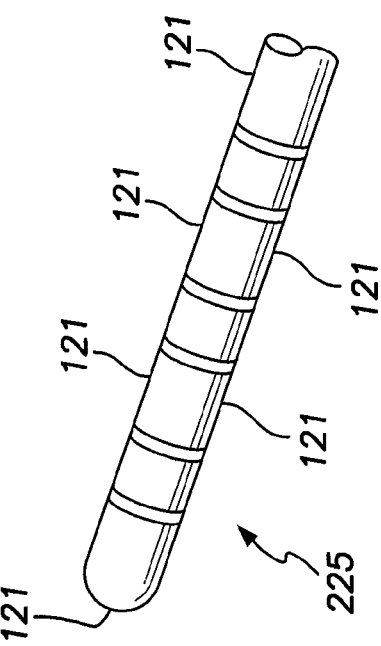
Figure 2A:
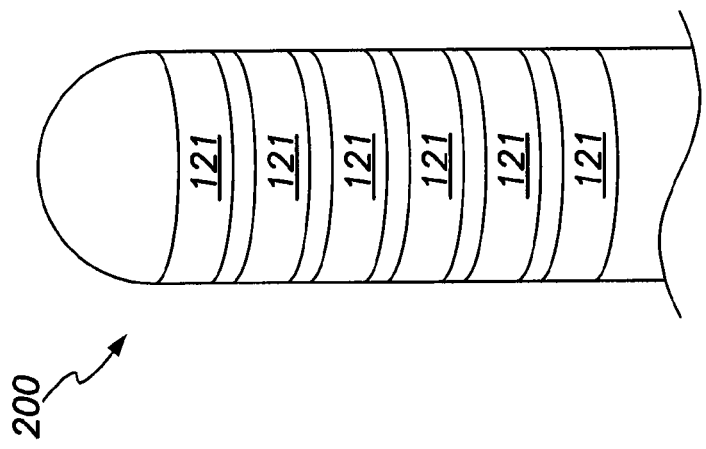

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION" which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different tonic and burst pulses on different stimulation electrodes 121a-d may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads 121a-d as is also known in the art. Various sets of parameters may define the pulse characteristics and pulse timing for the pulses applied to the various stimulation electrodes 121a-d. Although constant current pulse generating circuitry is contemplated for some embodiments, any other suitable type of pulse generating circuitry may be employed such as constant voltage pulse generating circuitry.

The controller 151, among other things, controls delivering a first current pulse configured as a tonic stimulation waveform to the at least one electrode, the tonic stimulation waveform configured to excite A-beta fibers of the nervous tissue; after a tonic-burst delay, delivering second current pulses configured as a burst stimulation waveform to at least one electrode, the burst stimulation waveform configured to excite C-fibers of the nervous tissue; and adjusting the tonic-burst delay between the tonic and burst stimulation waveforms to deliver the burst stimulation waveform during a refractory period of the A-beta fibers excited by the tonic stimulation waveform to avoid excitation of the A-beta fibers excited by the tonic stimulation waveform. The controller 151 controls sensing signals at the at least one electrode on the lead, and analyzing the signals to identify a C-fiber sensory action potential (C-fiber SAP) component of the signals. The controller 151 further comprises comprising adjusting the tonic-burst delay based on the C-fiber SAP component of the signals. The controller 151 adjusting operation includes adjusting the tonic-burst delay to reduce the C-fiber SAP component. The controller 151 further comprises analyzing a feature of interest from a morphology of the C-fiber SAP component over time, counting a number of occurrences of the feature of interest that occur within the C-fiber SAP component over a predetermined duration, comparing the number of occurrences to a prior number of occurrences, and adjusting the tonic-burst delay based on the comparing operation. The controller 151 further comprises analyzing the C-fiber SAP component to determine SAP activity level data for a present coupled tonic-burst therapy.

Memory 158 stores software to control operation of the controller 151 for coupled tonic/burst therapy as explained herein. The memory 151 also stores SAP signals, therapy parameters, SAP activity level data and the like.

For example, the memory 158 may save SAP activity level data for various different coupled tonic/burst therapies as applied over a short or extended period of time. A collection of SAP activity level data is accumulated for different therapies and may be compared to identify high, low and acceptable amounts of sensory activity for the C-fibers that result from different therapies.

A controller device 160 may be implemented to charge/recharge the battery 154 of the IPG 150 (although a separate recharging device could alternatively be employed) and to program the IPG 150 on the pulse specifications while implanted within the patient. Although, in alternative embodiments separate programmer devices may be employed for charging and/or programming the NS system 100. The controller device 160 may be a processor-based system that possesses wireless communication capabilities. Software may be stored within a non-transitory memory of the controller device 160, which may be executed by the processor to control the various operations of the controller device 160. A "wand" 165 may be electrically connected to the controller device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IPG 150. Optionally, in some embodiments, the wand 165 may comprise one or more temperature sensors for use during charging operations.

The user may initiate communication with the IPG 150 by placing the wand 165 proximate to the NS system 100. Preferably, the placement of the wand 165 allows the telemetry system of the wand 165 to be aligned with the far-field and/or near field communication circuitry 155 of the IPG 150. The controller device 160 preferably provides one or more user interfaces 168 (e.g., touchscreen, keyboard, mouse, buttons, or the like) allowing the user to operate the IPG 150. The controller device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different stimulation electrode 121*a-d* combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the controller device 160 may permit operation of the IPG 150 according to one or more coupled tonic/burst therapies to treat the patient. Each coupled tonic/burst therapies may include one or more sets of stimulation parameters of the pulse including pulse amplitude, pulse width, pulse frequency or inter-pulse period, pulse repetition parameter (e.g., number of times for a given pulse to be repeated for respective stimset during execution of program), biphasic pulses, monophasic pulses, etc. The IPG 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 3A:
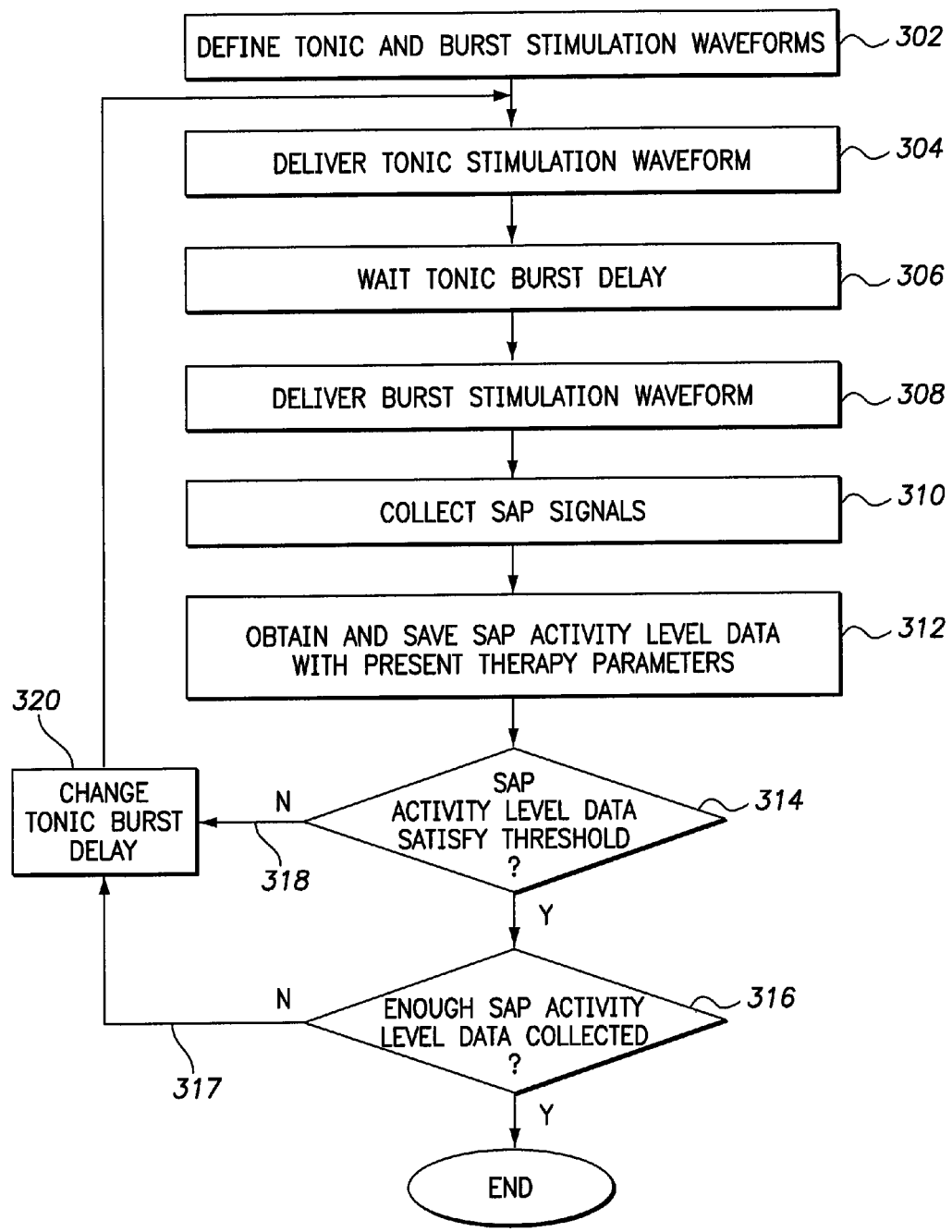
FIG. 3A illustrates a process for coupling tonic and burst stimulation of nervous tissue of a patient in accordance with embodiments herein.

FIG. 3A illustrates a process for coupling tonic and burst stimulation of nervous tissue of a patient in accordance with embodiments herein. The operations of FIG. 3A may be implemented by one or more processors, such as within an implantable pulse generator, external programmer, another external device and the like. The IPG, external programmer or other external device are coupled to a lead having at least one stimulation electrode that is implanted at a target position proximate to nervous tissue of interest.

At 302, the method defines a coupled tonic/burst therapy to be used, where the therapy includes a tonic stimulation waveform, a burst stimulation waveform and a tonic-burst delay imposed there between.

At 304, the method delivers a first current pulse configured as the tonic stimulation waveform. The first current pulse is delivered to at least one stimulation electrode on the lead. The tonic stimulation waveform is configured to excite at least a portion of the A-beta fibers at the target stimulation site. The tonic stimulation waveform may represent a monophasic waveform (with a positive or negative current pulse) or a biphasic waveform (with positive and negative pulses). When the tonic stimulation waveform is biphasic, a first pulse phase may be configured to capture at least a portion of the A-beta fibers to deliver a first pain relief. The biphasic tonic stimulation waveform may also include a second pulse phase configured to repolarize charge at a stimulation site (at which the tonic stimulation waveform is delivered). By repolarizing charge at the stimulation site, the second pulse phase limits an extent of A-beta fiber excitation (e.g., a degree to which, or amount of, the A-beta fibers are excited). The second pulse phase may be enlarged or decreased to increase or decrease an extent to which the first pulse phase of the biphasic tonic stimulation waveform excites the A-beta fibers.

At 306, the method waits a period of time defined by the tonic-burst delay. The tonic-burst represents a time period following the first current pulse until the beginning of the series of second current pulses. The tonic-burst delay is timed to deliver the burst stimulation waveform during a refractory period of the A-beta fibers, also referred to as the A-beta fiber refractory period. The burst stimulation waveform is timed to be delivered during the refractory period of the A-beta fibers, in order that the burst stimulation waveform does not excite (or at least generally avoids excitation of) A-beta fibers that were previously excited by the tonic stimulation waveform. By way of example, the series of current pulses defining the burst stimulation waveform may be delayed by a predetermined initial delay following the current pulse defining the tonic stimulation waveform, where the predetermined initial delay represents the initial tonic-burst delay that may be programmed by a clinician or automatically updated based upon feedback information collected by the IPG, external programmer or other external device.

Optionally, the initial tonic-burst delay may be set based on sensed signals indicative of the sensory action potentials experienced by the fast conduction fibers, such as the Group-A fibers. For example, sensory action potential signals may be measured from the A-beta fibers and a refractory period duration identified in the measured SAP signal. The initial tonic-burst delay may be set based on the A-beta fiber refractory period duration (e.g., as a percentage of the refractory period duration).

At 308, the method delivers a series of second current pulses configured as the burst stimulation waveform. The series of second current pulses is delivered to at least one electrode on the lead. The electrode or electrodes that deliver the burst stimulation waveform may be the same as, partially common with, or entirely distinct from the electrode or electrodes used to deliver the tonic relation waveform. For example, when the lead includes an array of electrodes, the tonic stimulation waveform delivered at 304 may be delivered to a first subset of the electrodes and the burst stimulation waveform delivered at 308 may be delivered to a second subset of the electrodes. The first and second subsets of the electrodes may be entirely unique from one another or may overlap to include some common elements while maintaining at least one unique electrode relative to each other.

The burst stimulation waveform is configured to excite at least a portion of the C-fibers at the target position. The burst stimulation waveform is defined by therapy parameters (e.g. pulse amplitude, pulse width, interpulse delay, number of pulses per series, series to series delay, etc.) to exhibits a burst morphology that does not excite "new" A-beta fibers that were not excited previously by the immediately preceding coupled tonic stimulation waveform (e.g., A-beta fibers that remain in an excitable or non-refractory state).

At 310, the method collects SAP signals, for a data collection window, indicative of the sensory action potential experienced by nervous tissue of interest at the target position. Electrodes on the lead may also be used for sensing to collect various sensed signals as described herein. The same electrodes may be used for sensing and stimulation. Alternatively, one group of electrodes may be used for sensing, while a different group of electrodes are used for stimulation. For example, the sensing electrodes may be spaced apart along the lead from the stimulation electrodes. Optionally, the sensing electrodes may be provided on a separate lead unique and distinct from the lead that includes the stimulation electrodes. For example, a conventional SCS lead may be positioned along the spinal column at a desired location in order to deliver coupled tonic-burst therapy at one or more stimulation sites of interest, while a separate sensing lead is provided. The separate sensing lead may include micro electrodes that are configured to be placed immediately adjacent fibers of interest, such as group-C fibers.

At 312, the method analyzes the SAP signal to obtain SAP activity level data indicative of whether the present coupled tonic/burst therapy is achieving a desired result. At 312, the method saves the SAP activity level data along with the parameters for the present coupled tonic/burst therapy, such as in a memory of the IPG, external programmer or other external device. The SAP activity level data and the associated therapy parameters may be saved in connection with delivering therapy based on multiple combinations of therapy parameters, thereby developing a therapy/sensitivity history for the patient. The therapy/sensitivity history indicates, among other things, a degree to which certain tonic/burst therapies inhibit sensory action potentials along slow conduction nerve fibers. The sensing and obtaining operations at 310 and 312 are described in more detail in connection with FIG. 3B.

At 314, the method determines whether the SAP activity level data determined at 312 satisfies one or more threshold criteria that are indicative of an acceptable pain relief efficacy. For example, when the SAP activity level data is indicative of an amount of activity exhibited by the slow conduction nerve fibers, the threshold criteria may represent a range or upper threshold for an acceptable amount of slow conduction nerve fiber activity. When the SAP activity level data exceeds the upper threshold limit or the upper limit of the range, the method determines that the coupled tonic/burst therapy is not adequately suppressing a patient's pain. At 314, when the SAP activity level data satisfies the threshold, flow moves to 316. Otherwise, flow moves along 318 to 320.

At 316, the method determines whether additional response data samples should be collected, such as additional SAP activity level data, in connection with alternative coupling relations (e.g. the length of the burst-tonic delay) between tonic and burst waveforms. For example, it may be desirable to obtain response data in connection with 5, 10 or more than 10 different coupled tonic/burst therapies, in order to derive a more complete understanding of a particular patient's neural fiber activity respond to different coupling relations of tonic and burst waveforms. When a sufficient amount of response data (e.g. enough SAP activity level data samples) is collected, the process ends. When more response data is desired, flow returns along 317 to 320.

At 320, the method adjusts the tonic-burst delay. For example, each time that the process cycles through the operation at 320, the tonic-burst delay may be increased or decreased by a predetermined amount. Optionally, the amount of change during each iteration through 320 may vary, such as with larger step changes made during initial iterations and smaller step changes made during later iterations. Optionally, the amount of change at 320 may be based on a difference between the SAP activity level data and the threshold. For example, when the SAP activity level data substantially exceeds the threshold, larger changes may be applied to the tonic-burst delay at 320. As the difference between the SAP activity level data and threshold decreases, the tonic-burst delay is changed by similarly/proportionally decreasing amounts. Following 320, flow returns to 304.

The operations at 304-320 are iteratively repeated to form a feedback loop in which the coupling relation (e.g. the tonic-burst delay) is continuously updated until obtaining a coupled tonic/burst therapy that inhibit spontaneous action potentials along the slow conduction fibers to no more than a select amount of activity.

Figure 3B:
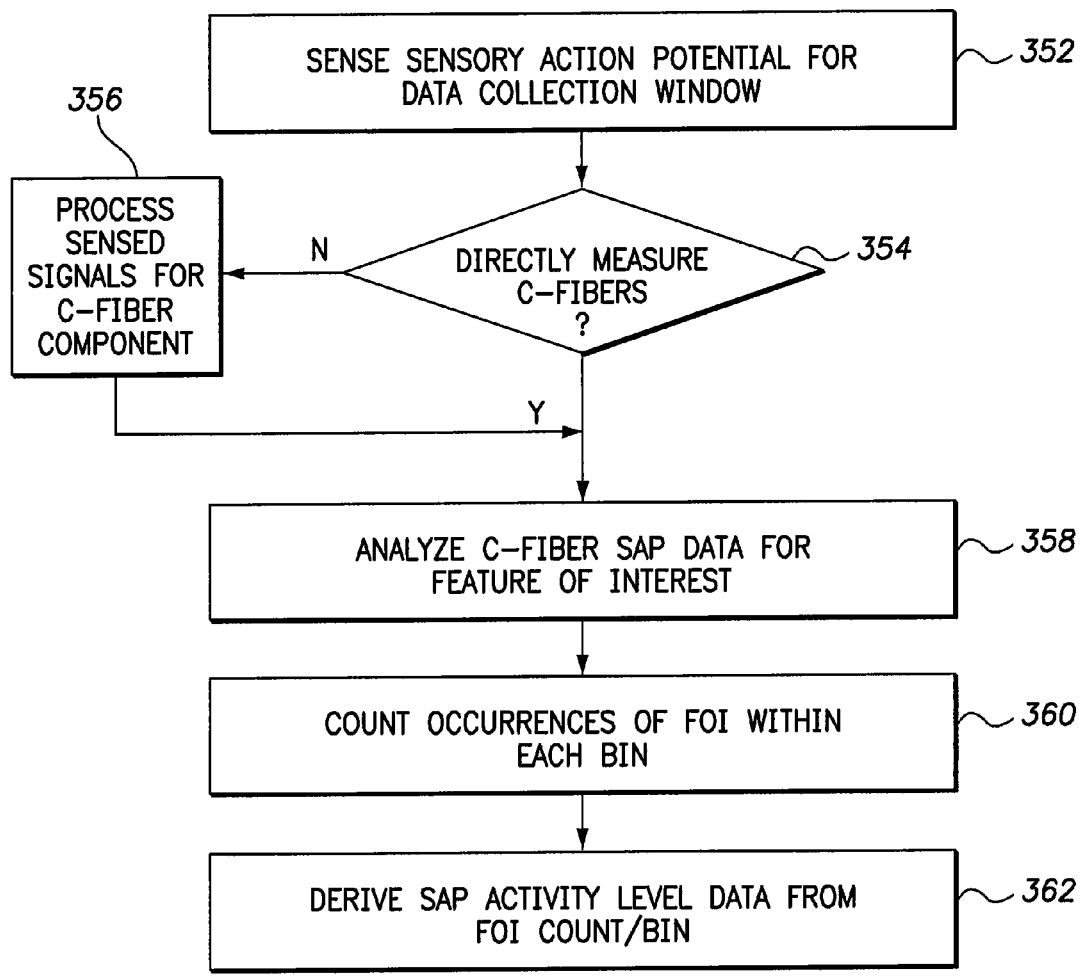
FIG. 3B illustrates a process for collecting and analyzing SAP signals to obtain SAP activity level data in connection with the operations of FIG. 3A in accordance with embodiments herein.

FIG. 3B illustrates a process for collecting and analyzing SAP signals to obtain SAP activity level data in connection with the operations 310 and 312 of FIG. 3A in accordance with embodiments herein. The operations FIG. 3B may be implemented by one or more processors, such as within an implantable pulse generator, and external programmer, an external device and the like. The IPG, external programmer or other external device are coupled to a lead having at least one stimulation electrode that is implanted at a target position proximate to nervous tissue of interest.

At 352, the method utilizes one or more electrodes on one or more leads implanted proximate to the target site to sense SAP signals indicative of a sensory action potential of the nervous tissue of interest. The SAP signals are collected over a data collection window (e.g. a few seconds, a few minutes or otherwise) and saved in memory (e.g., memory 158). The SAP signals are sensed between therapies such that no tonic or burst stimulation is delivered while collecting SAP signals. The electrodes at which the SAP signals are sensed may be the same as, partially common with, or entirely distinct from the electrode or electrodes used to deliver coupled tonic/burst therapy. The electrodes may represent micro-electrodes positioned to directly sense signals from C-fibers. Optionally, the electrodes may represent electrodes on a conventional SCS lead that are positioned and configured to sense sensory action potentials from various fibers within the spinal column, such as the A-beta fibers.

At 354, the method determines whether the SAP signal represents a signal that directly measures the sensory action potential of the slow conducting fibers of interest, such as C-fibers. By way of example, when micro electrodes are positioned immediately adjacent C-fibers, the sensed SAP signal would represent a direct measure of the sensory action potential of the slow conducting fibers of interest. Alternatively, when a conventional lead with larger electrodes are positioned in the dorsal column, the larger electrodes are not positioned immediately adjacent C-fibers. Instead, the larger electrodes measure a "composite" sensory action potential from multiple types of fibers in the dorsal column, where the composite SAP includes SAP components associated with fast conducting fibers and SAP components associated with slow conducting fibers. For example, the composite SAP signal may include an A-alpha fiber SAP component, A-beta fiber SAP component, an A-delta fiber SAP component, a B-fiber SAP component, a C-fiber SAP component and the like.

At 354, when the method determines whether the sensed SAP signal corresponds directly to the slow conduction SAP component (e.g. the C-fiber component) and thus represents, slow conduction SAP data flow moves to 358. Otherwise, when the method determines at 354 that the sensed SAP signal is a composite SAP signal that does not correspond directly to the slow conduction SAP component, flow moves to 356.

At 356, the method processes the sensed composite SAP signal to identify the slow conduction SAP component and generates slow conduction SAP data based thereon. For example, a fast Fourier transform may be applied to the composite SAP signal to separate the frequency components therein. Certain composite frequency components of the sensed composite SAP signal entirely or primarily are generated by slow conduction nerve fibers (e.g., C-fibers). Thus, the composite SAP signal may be converted to the frequency domain through an FFT conversion to form FFT converted SAP data. The slow conduction frequency components of interest from the FFT converted SAP data may be isolated, such as through filtering. Next, the slow conduction frequency components of interest from the FFT converted SAP data may be returned at 358 as slow conduction SAP data in the frequency domain. Optionally, the slow conduction frequency components in the frequency domain may be converted through an inverse fast Fourier transform back to the time domain to form slow conduction SAP data in the time domain.

At 358, the method analyzes the slow conduction SAP data (in the time domain or frequency domain) for one or more features of interest. For example, the feature of interest may represent a number of positive and negative peaks within the slow conduction SAP data for a select period of time. When processing the slow conduction SAP data in the time domain, the operation at 358 may include a binning operation, in which the slow conduction SAP data is segmented into a series of temporal bins. Each temporal bin may include one or more occurrences of the feature of interest (e.g. spikes or peaks).

At 360, the method counts a number of occurrences of the feature of interest (FOI) within each temporal bin. For example, when analyzing the slow conduction SAP data in the time domain, each temporal bin may correspond to ½-1 second of slow conduction SAP data. The slow conduction SAP data exhibits a number of spikes/peaks within each temporal bin, where the number of spikes/peaks is indicative of, and proportional to, an amount of sensory activity conveyed along the corresponding slow conduction nervous fibers. As more sensory activity is conveyed along the slow conduction nervous fibers, the number of spikes/peaks within the temporal bins increase. Conversely, as less sensory activity is conveyed along the slow conduction nervous fibers, the number of spikes/peaks within the temporal bins decrease.

At 362, the method derives SAP activity level data from the count for the temporal bins. For example, the SAP activity level data may indicate that the number of spikes/peaks are within an acceptable upper limit/range or below an acceptable threshold, thereby indicating that a present coupled tonic/burst therapy is acceptable. Alternatively, the SAP activity level data may indicate that the number of spikes/peaks is not within an acceptable range or exceeds an upper limit/threshold, thereby indicating that the present coupled tonic/burst therapy is not achieving a desired affect and warrants modification. The SAP activity level data is stored in combination with the corresponding present coupled tonic/burst therapy. Optionally, additional information regarding the patient's condition may be stored with the SAP activity level data (e.g. heart rate, physical activity level and the like). The SAP activity level data is used in accordance with embodiments herein to adjust the tonic-burst delay within a coupled tonic/burst therapy.

As a further option, the SAP activity level data may give additional information about a nature (e.g., amount and/or direction) of the change in the sensory activity. For example, the SAP activity level data may indicate that the slow conduction SAP data is exhibiting a certain amount of change (e.g. percentage) in sensory activity (e.g. a 5% increase over the past hour, 10% increase over the past day. The amount of change may be characterized as a "large" or "small" decrease or increase relative to an average level of activity or otherwise. For example, the method may save SAP activity level data over an extended period of time (e.g. several days, several weeks or longer). The SAP activity level data may be averaged or otherwise statistically analyzed to determine a mathematical indicator of certain characteristics of the SAP activity level data. For example, the indicator may denote a baseline amount of sensory activity. The indicator may denote levels of sensory activity associated with known or periodic behavior where such level of reactivity are acceptable and do not warrant modification of the coupled tonic/burst therapy.

The operations of FIG. 3B may be repeated throughout operation periodically based upon inputs from a patient or clinician, periodically based upon an operation of the IPG and the like.

Figure 7:
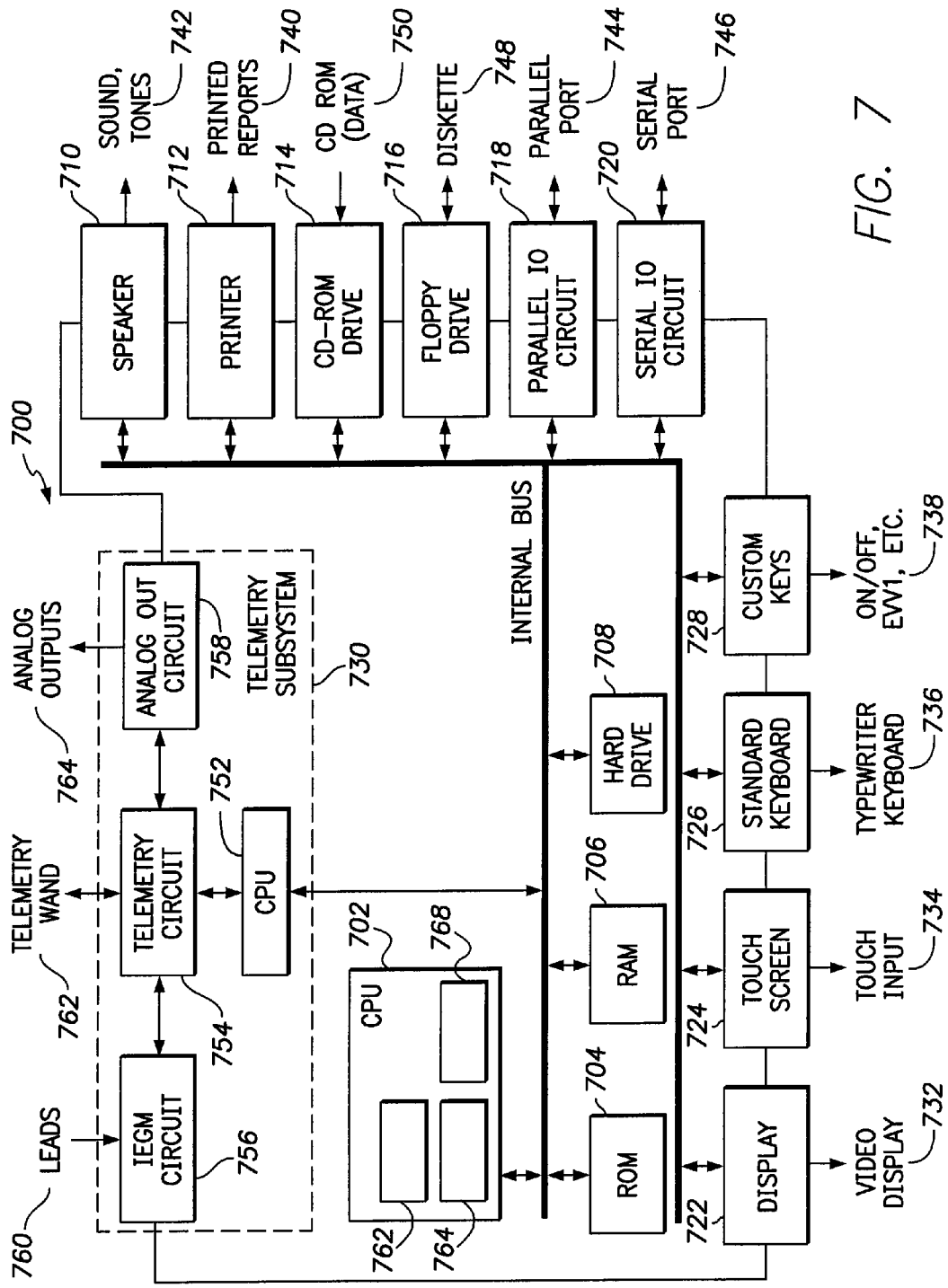
FIG. 7 illustrates a functional block diagram of an embodiment of an electronic control unit (ECU) that is operated in accordance with the processes described herein to analyze SAP signals and to interface with one or more IPGs and/or leads with electrodes positioned at stimulation sites to deliver coupled tonic/burst therapies and/or sense sensory action potential signals.

FIG. 7 illustrates a functional block diagram of an embodiment of an electronic control unit (ECU) 700 that is operated in accordance with the processes described herein to analyze SAP signals and to interface with one or more IPGs and/or leads with electrodes positioned at stimulation sites to deliver coupled tonic/burst therapies and/or sense sensory action potential signals. The ECU 700 may be a workstation, a portable computer, a PDA, a cell phone and the like. The ECU 700 includes an internal bus that connects/interfaces with a Central Processing Unit (CPU) 702, ROM 704, RAM 706, a hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus is an address/data bus that transfers information between the various components described herein. The hard drive 708 may store operational programs as well as data, such as waveform templates and detection thresholds.

The CPU 702 typically includes a microprocessor, a micro-controller, or equivalent control circuitry, and may interface with an IPG and/or lead. The CPU 702 may include RAM or ROM memory, logic and timing circuitry, state machine circuitry, and I/O circuitry to interface with the IPG and/or lead. The display 722 (e.g., may be connected to the video display 732). The touch screen 724 may display graphic information relating to the CNS 110. The display 722 displays various information related to the processes described herein. The touch screen 724 accepts a user's touch input 734 when selections are made. The keyboard 726 (e.g., a typewriter keyboard 736) allows the user to enter data to the displayed fields, as well as interface with the telemetry subsystem 730. Furthermore, custom keys 728 turn on/off 738 (e.g., EVVI) the ECU 700. The printer 712 prints copies of reports 740 for a physician to review or to be placed in a patient file, and speaker 710 provides an audible warning (e.g., sounds and tones 742) to the user. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750.

The CPU 702 is configured to analyze SAP signals collected by one or more electrodes. The CPU 702 includes a therapy circuit module 764 that is configured to control delivery of a first current pulse configured as a tonic stimulation waveform to the at least one electrode. The tonic stimulation waveform is configured to excite A-beta fibers of the nervous tissue. The therapy circuit module 746 is further configured to, after a tonic-burst delay, control delivery of second current pulses configured as a burst stimulation waveform to at least one electrode. The burst stimulation waveform is configured to excite C-fibers of the nervous tissue.

The CPU 702 also includes a delay adjustment circuit module 762 that adjusts the tonic-burst delay between the tonic and burst stimulation waveforms to deliver the burst stimulation waveform during a refractory period of the A-beta fibers excited by the tonic stimulation waveform to avoid excitation of the A-beta fibers excited by the tonic stimulation waveform, as explained herein. For example, the delay adjustment circuit module 762 may adjust the tonic-burst delay to reduce the C-fiber SAP component The CPU 702 also includes an SAP analysis circuit module 768 that receives sensed SAP signals from at least one electrode on the lead, and analyzes the SAP signals to identify a C-fiber sensory action potential (C-fiber SAP) component of the signals. For example, the SAP analysis circuit module 768 may determine an amount to adjust the tonic-burst delay based on the C-fiber SAP component of the signals. The SAP analysis circuit module 768 may adjust analyze a feature of interest from a morphology of the C-fiber SAP component over time, count a number of occurrences of the feature of interest that occur within the C-fiber SAP component over a predetermined duration, compare the number of occurrences to a prior number of occurrences, and determine and amount to adjust the tonic-burst delay based on the comparing operation. The SAP analysis circuit module 768 may analyze the C-fiber SAP component to determine SAP activity level data for a present/current coupled tonic/burst therapy. The SAP activity level data is saved in memory with the associated therapy parameters.

In accordance with at least one embodiment, SAP activity level data is collected in connection with a plurality of coupled tonic-burst therapies. The SAP activity levels are compared and a select one of the SAP activity levels is chosen. For example, a lowest SAP activity level may be chosen. Alternatively, a most frequent SAP activity level may be chosen. Alternatively, a lowest or most frequent SAP activity level within a select range or below an upper limit may be chosen. A coupled tonic-burst therapy associated with the chosen SAP activity level is identified from the therapies stored in memory. The delay adjustment circuit module 762 adjusts the tonic-burst delay to correspond to the identified coupled tonic-burst therapy.

The telemetry subsystem 730 includes a central processing unit (CPU) 752 in electrical communication with a telemetry circuit 754, which communicates with both an SAP circuit 756 and an analog out circuit 758. The circuit 756 may be connected to leads 760. The circuit 756 may also be connected to implantable leads to receive and process SAP signals. Optionally, the SAP signals sensed by the leads may be collected by the CNS 110 and then transmitted, to the ECU 700, wirelessly to the telemetry subsystem 730 input.

The telemetry circuit 754 is connected to a telemetry wand 762. The analog out circuit 758 includes communication circuits to communicate with analog outputs 764. The ECU 700 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 700 to the CNS 110.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

Figure 4:
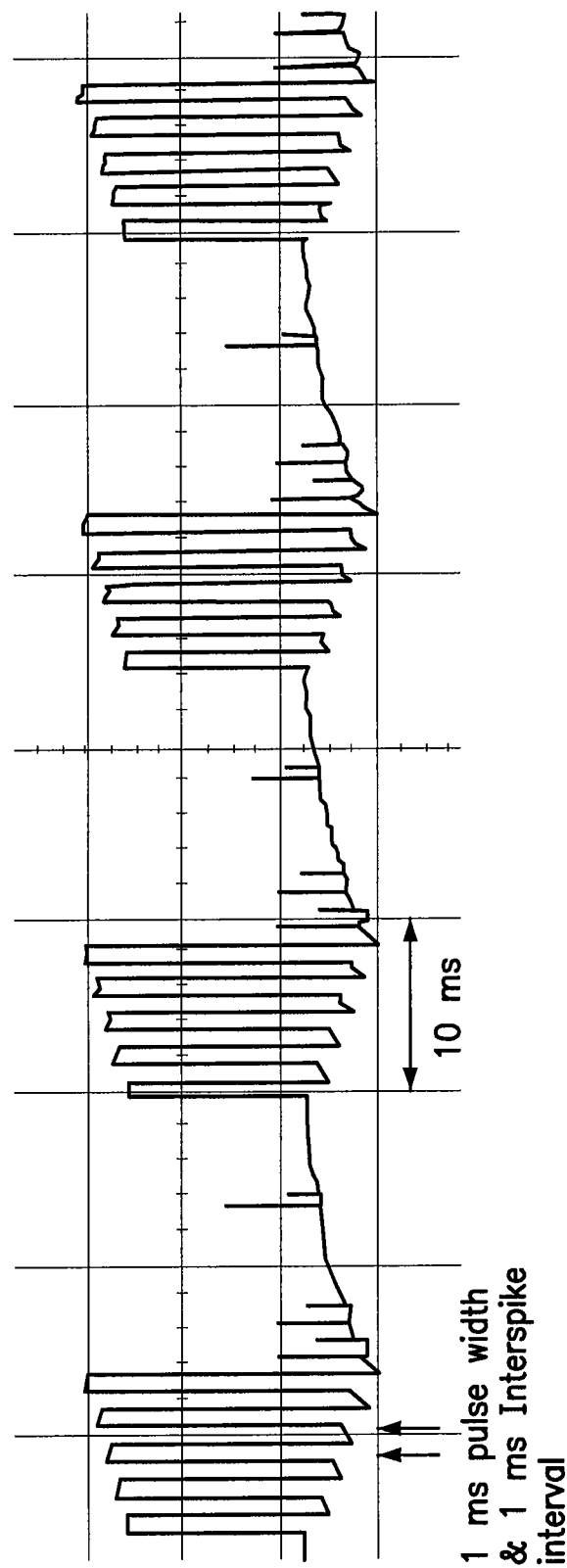
FIG. 4 illustrates a group of burst stimulation waveforms utilized in accordance with embodiments herein.

FIG. 4 illustrates a group of burst stimulation waveforms utilized in accordance with embodiments herein. The horizontal axis represents time in milliseconds, while the vertical axis represents current or voltage. An exemplary burst stimulation waveform may include a series of current pulses (e.g. five sub-pulses) delivered at a rate of 500 Hz per burst. Each pulse may have a pulse width of 1 ms with a 1 ms interval between adjacent pulses (e.g. the inter-spike interval). By way of example, the total pulse width for a pulse burst may be 10 ms. As an example, successive pulse bursts may be spaced apart by a select interval, such as 15 ms.

Figure 5:
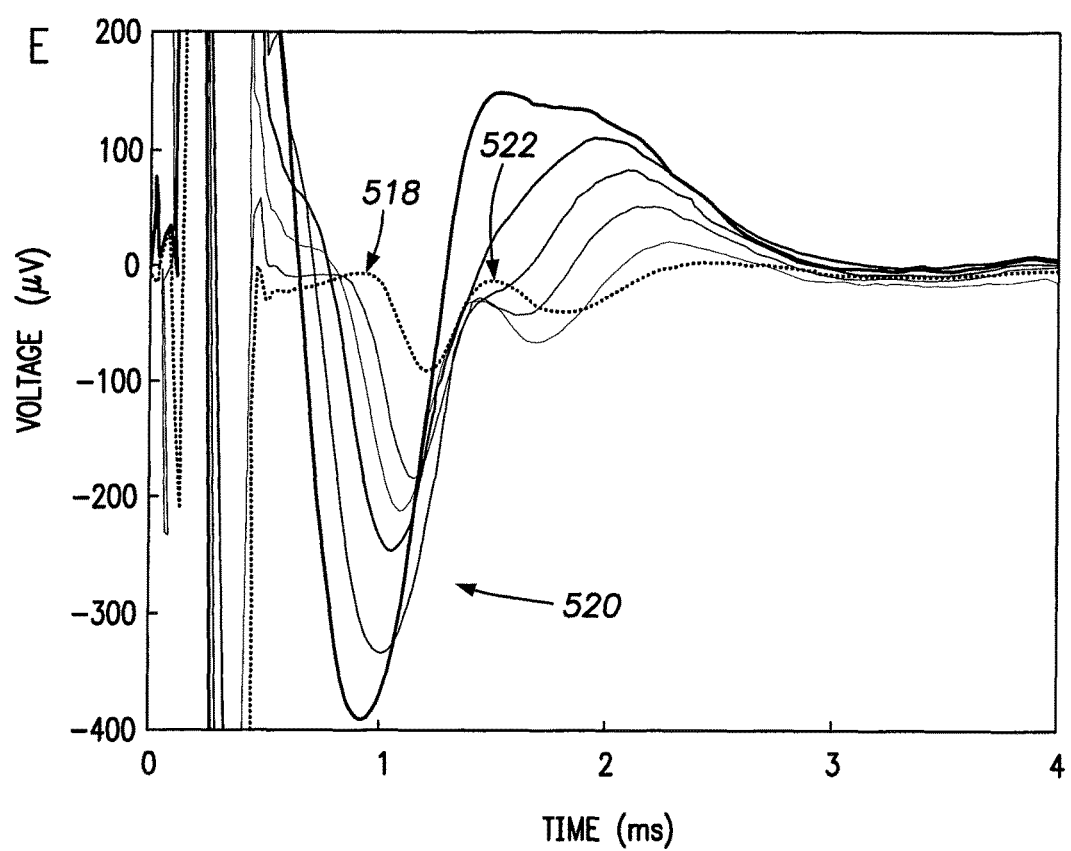
FIG. 5 illustrates a group of composite SAP signals indicative of evoked compound action potentials (ECAP) collected during a sensing operation in accordance with embodiments herein.

FIG. 5 illustrates a group of composite SAP signals indicative of evoked compound action potentials (ECAP) collected during a sensing operation in accordance with embodiments herein. The horizontal axis represents time in milliseconds, while the vertical axis represents voltage in micro volts. A tonic burst waveform is delivered in the first 0.8 ms, such as from a conventional SCS electrode into the dorsal column. The sensed ECAP signals are sensed between 0.8 ms to 3.0 ms. Each of the ECAP signals represents a composite SAP signal including action potential components conveyed along the A, B and Group C-fibers. Action potentials propagate along the A, B and Group C-fibers at different speeds because the A, B and Group C-fibers exhibit different conduction velocities. Accordingly, the sensed ECAP signals exhibit a morphology having various features of interest (generally denoted at deflection points 518, negative peaks 520 and positive peaks 522) that are contributed by, and indicative of, action potentials associated with corresponding A, B, or Group C-fibers. For example, the initial (largest) peaks or spike (generally denoted at the deflection points 520) in the ECAP signal is attributed by, and indicative of, the action potential component(s) conveyed by the Group A fibers. The second positive peak or spike (generally denoted at 522) is attributed by, and indicative of, the action potential component(s) conveyed by the Group C-fibers. The ECAP signals return to a baseband value (around approximately 0 micro volts) at the 3 ms point in time, which may be an indicator of the action potential cycle.

Figure 6:
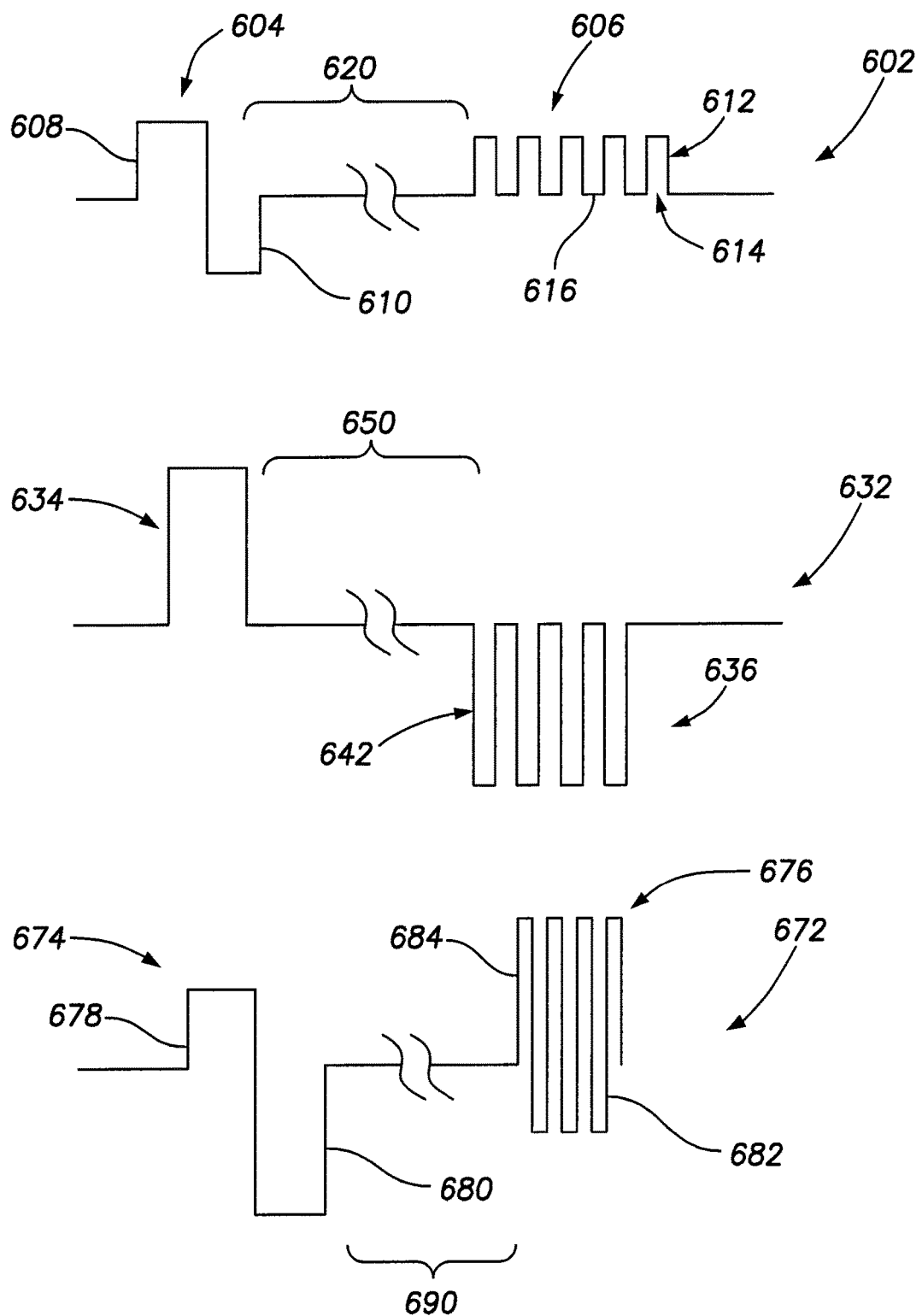
FIG. 6 illustrates examples of coupled tonic/burst therapies implemented in accordance with embodiments herein.

FIG. 6 illustrates examples of coupled tonic/burst therapies implemented in accordance with embodiments herein. The coupled tonic/burst therapy 602 includes a tonic stimulation waveform 604 and a burst stimulation waveform 606. The tonic stimulation waveform 604 includes a positive phase pulse 608 and a negative phase pulse 610. The burst stimulation waveform 606 includes a series of positive phase pulses 612. The pulses 612 have a programmed pulse width 614 and are spaced apart by a pulse-to-pulse interval 616.

The tonic stimulation waveform 604 is a biphasic waveform with a first positive phase pulse 608 (0.5 ms pulse width for each phase) that captures at least a portion of the Group A-beta fibers thereby delivering a first pain relief. The second/negative phase pulse 610 repolarizes the charges on the stimulation site to limit excitation of pain related neural fibers. Following a tonic-burst delay 620, a burst stimulation waveform 606 is delivered.

The pulses 612 of the burst stimulation waveform 606 may have a lower amplitude and/or lower energy that the pulses 608, 610 of the tonic stimulation waveform 604, in order to prevent stimulation of an additional portion of the Group A-beta fibers of the SC while the top portion of the Group A-beta fibers remain in the refractory state. The burst stimulation waveform 606 is timed and delivered at a select amplitude, in order to capture nervous fibers at a deeper layer of the spinal column but also avoid the overstimulation of the top layer of SC (top lay of SC is still in refractory period). By way of example, each pulse 612 may have a pulse width of 1 ms with a 1 ms pulse to pulse interval 616 there between.

Another coupled tonic/burst therapy 632 is illustrated with a monophasic tonic stimulation waveform 634 followed by a burst stimulation waveform 636 that includes a series of negative pulses 642. The amplitudes of the negative pulses 642 may be greater than the amplitude of the monophasic pulse 634. The tonic burst delay 650 may be longer or shorter than the delay 620.

A coupled tonic/burst therapy 672 is illustrated to include a biphasic tonic stimulation waveform 674 and, following a delay 690, a burst stimulation waveform 676. The positive pulse 678 of the tonic stimulation waveform 674 has a smaller amplitude than the negative pulse 680. It may be desirable to adjust the amplitudes of the positive and negative pulses 678 and 680 within the tonic stimulation waveform 674 to capture a desired amount/portion of the A-fibers, while repolarizing the stimulation site to limit or prevent excessive capture of an undesired amount/portion of the A-fibers. The burst stimulation waveform 676 includes positive and negative pulses 684 and 682. The amplitudes and/or pulse widths of the pulses 684 and 682 may differ from one another or be the same, in order to inhibit a desired amount/portion of the sensory activity for the C-fibers.

The controller 160 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controllers 151 and the controller device 160 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controllers and the controller device may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

What is claimed is:

1. A method for controlling burst stimulation of nervous tissue of a patient, the method comprising:
   providing a lead having at least one electrode on the lead configured to be implanted at a target position proximate to nervous tissue of interest;
   delivering a first current pulse configured as a tonic stimulation waveform to the at least one electrode, the tonic stimulation waveform configured to excite A-beta fibers of the nervous tissue;
   after a tonic-burst delay, delivering second current pulses configured as a burst stimulation waveform to the at least one electrode, the burst stimulation waveform configured to excite C-fibers of the nervous tissue; and
   adjusting the tonic-burst delay between the tonic and burst stimulation waveforms to deliver the burst stimulation waveform during a refractory period of the A-beta fibers excited by the tonic stimulation waveform to avoid excitation of the A-beta fibers excited by the tonic stimulation waveform.

2. The method of claim 1, wherein the current pulses of the burst stimulation waveform are delayed by a predetermined initial delay following the current pulse of the tonic stimulation waveform, the predetermined initial delay representing the tonic-burst delay and being programmed by a clinician.

3. The method of claim 1, wherein the tonic stimulation waveform represents a biphasic waveform and the burst stimulation waveform represents a series of monophasic pulses.

4. The method of claim 1, wherein the tonic stimulation waveform is biphasic with first and second phase pulses, the first phase pulse configured to capture at least a portion of the A-beta fibers to deliver a first pain relief, the second phase pulse configured to repolarize charge at a stimulation site to limit excitation of A-beta fibers.

5. The method of claim 1, further comprising sensing signals at the at least one electrode on the lead, and analyzing the signals to identify a C-fiber sensory action potential (C-fiber SAP) component of the signals.

6. The method of claim 5, further comprising adjusting the tonic-burst delay based on the C-fiber SAP component of the signals.

7. The method of claim 6, wherein the adjusting operation includes adjusting the tonic-burst delay to reduce the C-fiber SAP component.

8. The method of claim 5, further comprising analyzing a feature of interest from a morphology of the C-fiber SAP component over time, counting a number of occurrences of the feature of interest that occur within the C-fiber SAP component over a predetermined duration, comparing the number of occurrences to a prior number of occurrences, and adjusting the tonic-burst delay based on the comparing operation.

9. The method of claim 5, further comprising analyzing the C-fiber SAP component to determine SAP activity level data for a present coupled tonic-burst therapy.

10. The method of claim 1, wherein the at least one electrode comprises a plurality of electrodes; and wherein the delivering operation comprises delivering the tonic stimulation waveform to a first sub-set of the electrodes and the burst stimulation waveform to a second sub-set of the electrodes, the first and second sub-sets have at least one unique electrode relative to each other.

11. The method of claim 1, wherein the at least one electrode includes a microelectrode located immediately adjacent C-fibers, the method further comprising sensing a C-fiber sensory action potential (SAP) directly at the microelectrode and performing an iterative feedback loop to adjust at least one therapy parameter for a coupled tonic-burst therapy based on the C-fiber SAP.

12. A system for coupling burst and tonic stimulation, the system comprising:
   a lead having at least one stimulation electrode, the lead configured to be implanted at a target position proximate to nervous tissue of interest; and
   an implantable pulse generator (IPG) coupled to the lead, the IPG configured to:
      deliver a first current pulse configured as a tonic stimulation waveform to the at least one electrode, the tonic stimulation waveform configured to excite A-beta fibers of the nervous tissue;
      after a tonic-burst delay, deliver second current pulses configured as a burst stimulation waveform to the at least one electrode, the burst stimulation waveform configured to excite C-fibers of the nervous tissue; and
      adjust the tonic-burst delay between the tonic and burst stimulation waveforms to deliver the burst stimulation waveform during a refractory period of the A-beta fibers excited by the tonic stimulation waveform to avoid excitation of the A-beta fibers excited by the tonic stimulation waveform.

13. The system of claim 12, wherein the lead includes a plurality of electrodes, and the IPG is configured to deliver the tonic stimulation waveform to a first sub-set of the electrodes and the burst stimulation waveform to a second sub-set of the electrodes, the first and second sub-sets have at least one unique electrode relative to each other.

14. The system of claim 12, wherein the at least one electrode includes a microelectrode configured to be located immediately adjacent C-fibers and configured to sense a C-fiber sensory action potential (SAP) directly at the microelectrode.

15. The system of claim 11, wherein the at least one electrode on the lead senses signals and the processor analyzes the signals to identify a C-fiber sensory action potential (C-fiber SAP) component of the signals.

16. The system of claim 15, wherein the processor is configured to adjust the tonic-burst delay based on the C-fiber SAP component of the signals.

17. The system of claim 15, wherein the processor is configured to adjust the tonic-burst delay to reduce the C-fiber SAP component.

18. The system of claim 15, wherein the processor is configured to analyze a feature of interest from a morphology of the C-fiber SAP component over time, count a number of occurrences of the feature of interest that occur within the C-fiber SAP component over a predetermined duration, compare the number of occurrences to a prior number of occurrences, and adjust the tonic-burst delay based on the comparing operation.

19. The system of claim 15, wherein the processor is configured to analyze the C-fiber SAP component to determine SAP activity level data for a present coupled tonic-burst therapy.

20. The system of claim 11, wherein the at least one electrode comprises a plurality of electrodes; and wherein the processor is configured to deliver the tonic stimulation waveform to a first sub-set of the electrodes and the burst stimulation waveform to a second sub-set of the electrodes, the first and second sub-sets have at least one unique electrode relative to each other.

* * * * *